United States Patent [19]

Steer

[11] Patent Number: 4,781,708

[45] Date of Patent: Nov. 1, 1988

[54] TELESCOPING COUPLING FOR AN OSTOMY APPLIANCE

[75] Inventor: Peter L. Steer, Reigate, England

[73] Assignee: Craig Medical Products Limited, Sussex, England

[21] Appl. No.: 38,464

[22] Filed: Apr. 13, 1987

Related U.S. Application Data

[63] Continuation of Ser. No. 849,605, Apr. 8, 1986, abandoned.

[30] Foreign Application Priority Data

Apr. 10, 1985 [GB] United Kingdom ............... 85098168

[51] Int. Cl.⁴ .............................................. A61F 5/44
[52] U.S. Cl. .................................... 604/338; 604/342
[58] Field of Search ................................ 604/332–345; 285/302

[56] References Cited

U.S. PATENT DOCUMENTS 4,419,100 12/1983 Alexander ........................... 604/339
4,460,363 7/1984 Steer et al. ........................... 604/336
4,464,178 8/1984 Dalton ............................... 604/180

FOREIGN PATENT DOCUMENTS 1571657 7/1980 United Kingdom .
1583027 1/1981 United Kingdom .
2101249 1/1983 United Kingdom .
2115288 9/1983 United Kingdom ............... 604/339
2163350 2/1986 United Kingdom .

*Primary Examiner*—Dalton L. Truluck
*Assistant Examiner*—J. L. Kruter
*Attorney, Agent, or Firm*—Lawrence S. Levinson; Sanford J. Asman

[57] ABSTRACT

For any ostomy appliance, a body-side ostomy member includes a medical grade adhesive pad and a coupling having one part captive to but telescopically slidable relative to another part to provide access for the fingers or thumb of a wearer beneath a lateral flange of the coupling, when the parts are spaced from one another.

This allows an ostomy coupling to be secured together without applying undue pressure to the sensitive body area of the wearer.

8 Claims, 3 Drawing Sheets

Fig. 5.

TELESCOPING COUPLING FOR AN OSTOMY APPLIANCE

This is a continuation of co-pending application Ser. No. 849,605 filed on Apr. 8, 1986 now abandoned.

BACKGROUND OF THE INVENTION

This invention relates to an ostomy appliance and to a body side ostomy member for use in an ostomy appliance.

Ostomy appliances in which an ostomy bag is connected to a medical grade adhesive pad via a pair of interengageable coupling elements, one element being on the pad and one on the bag are known. The pad is usually adhesively attached to the wearer and need not be disturbed for some days. One successful system is described in British Pat. No. 1,571,657 entitled Coupling for Joining an Ostomy Bag to a Pad which issued to P. L. Steer, et al. Such an arrangement allows a bag to be removed and replaced without detaching the pad from the body of the wearer, thereby allowing the bag to be emptied or drained.

Some wearers suffer pain or discomfort when reattaching a bag or attaching a fresh bag, because it is normally necessary to apply some force in a direction towards the wearer's body in order to interengage the coupling elements. As the peristomal area and the stoma are usually tender, any force applied to the wearer's body gives rise to discomfort or pain. Efforts have been made to reduce or solve this problem by devising constructions which are intended to allow the wearer to place his fingers or thumbs behind a part of the appliance, with the aim of preventing some or all of the force applied to connect the coupling elements from being applied to the stomal region. One suggestion is described in Great Britain Patent Application No. 2,115,288 A entitled Ostomy Appliance and Faceplate Attachment which filed by B. S. Alexander of Sept. 13, 1982. This attempted solution itself suffers from various defects. First, the area of the stomal orifice is restricted, by the inner periphery of a thin annular flexible resilient web which extends into and restricts the aperture. The inner edge of this web, being rather sharp, causes considerable pain if it contacts the exposed stoma. Second, the use of a thin web in the attachment of the bag to the body side pad (also sometimes called a faceplate) has the result that when the wearer is upright the bag tends to drag or droop downwardly. The perception of the user is that the whole arrangement is less compact and secure than other kinds of ostomy appliances. Thirdly, the arrangement inevitably has crannies in which feces can collect.

SUMMARY OF THE INVENTION

According to one aspect of the present invention, there is provided a body side ostomy member which includes a medical grade adhesive pad having, or which can be provided with, a stomal aperture, and a coupling having one part captive to, but telescopically slidable to, another part to provide access for the fingers or thumb of a wearer beneath a lateral flange of the coupling when the parts are spaced from one another.

According to another aspect of the present invention, there is provided a body side ostomy member for attachment to a pad of medical grade adhesive, the member including one part having a lateral flange and a coupling element, said one part being slidable on, and relative to, another part, in a direction towards and away from the body of the wearer to provide a space between the specified parts to enable a thumb or fingers to be placed therebetween.

According to a more specific aspect of the invention, a body side ostomy member, for use in attaching an ostomy bag to a wearer, includes:
   (a) a medical grade adhesive pad having, or which can be provided with, a stomal aperture,
   (b) a coupling having at least two parts, in which
   (c) one of the parts includes a flange attached to a side of the pad remote from the body, the flange having a stomal aperture and there being a wall (herein called a first wall) of closed loop from surrounding the stomal aperture and extending from the flange in a direction away from the paid, and in which
   (d) another of the parts has a wall (herein called a second wall) of closed loop form surrounding and slidable relative the first wall over a limited extent, the second wall being connected to and integral with a laterally extending flange carrying one element of a pair of mutually engageable coupling element.

The stomal orifice will usually be substantially circular and the first and second walls may be substantially cylindrical, but walls of oval or polygonal or any other closed loop shape which defines a stomal aperture may be used. The interengaging coupling elements may be as disclosed and illustrated in British Pat. No. 1,571,657 entitled Coupling for Joining an Ostomy Bag to a Pad which issued to P. L. Steer, et al. referred to above. Other known interengaging coupling elements, e.g., those shown in British Pat. Nos. 1,583,027 and 2,101,249 may also be used.

In a preferred embodiment of the present invention, the first and second walls are located within one another for telescopic sliding movement, and the movement is limited by a particularly convenient arrangement which also serves a sealing or anti-leakage function. The innermost wall is provided with an outwardly extending resilient flexible peripheral seal strip, and the outermost wall is provided at its other end with an inwardly extending resilient flexible peripheral seal strip. Each of these seal strips extends towards, and its distal portion engages, the confronting surface of the other wall. Preferably, the walls are substantially coaxial cylinders sliding one within the other, and the inner wall is connected to (or integral with) the flange which is secured to the medical grade adhesive pad. In the telescopically extended condition of the two walls, the presence of the peripheral strips prevents the two walls, and hence the two parts of the body side member, from being separated, In other words, the walls are held captive to each other once assembled.

BRIEF DESCRIPTION OF THE DRAWINGS

In the Drawing:

FIG. 5 is an axial cross-section illustrating the part 12 cooperating with a bag side ostomy coupling member.

DETAILED DESCRIPTION OF THE PREFERRED EMBODIMENT

In FIGS. 1-4, for simplicity of illustration, only those portions of the device on one side of a central axis are shown, it being understood that in the preferred embodiment of the invention the device is symmetrical about an axial line constituting the center line of the stomal orifice. In its preferred version, the body side member according to the invention is symmetrical about a central axis, but an oval or other shaped configuration rather than a circular configuration, may be equally well employed, and the scope of the invention includes oval and other non-circular configurations.

Figure 1:
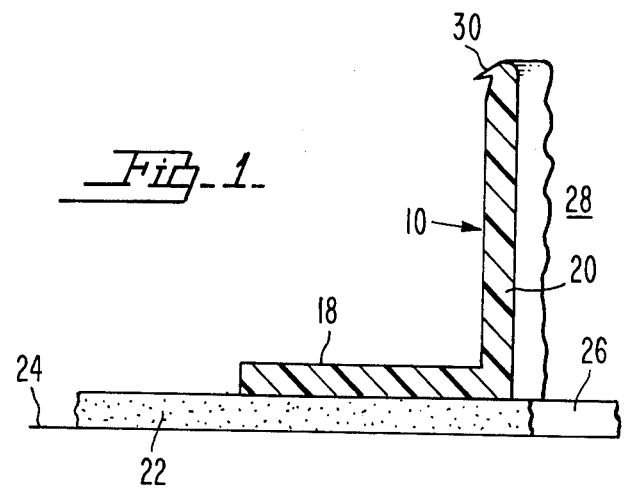
FIG. 1 is a partial axial cross-section through one part of a body side member of the ostomy appliance of the present invention.
Figure 2:
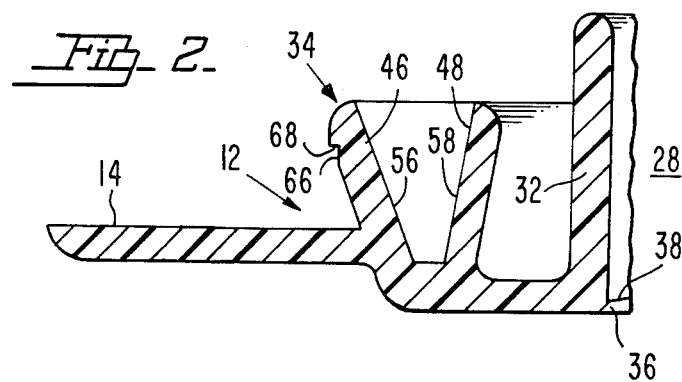
FIG. 2 is an axial section through part of a second part of a body side member of the ostomy appliance of the present invention, the said second part being intended for cooperation with the first part shown in FIG. 1.
Figure 3:
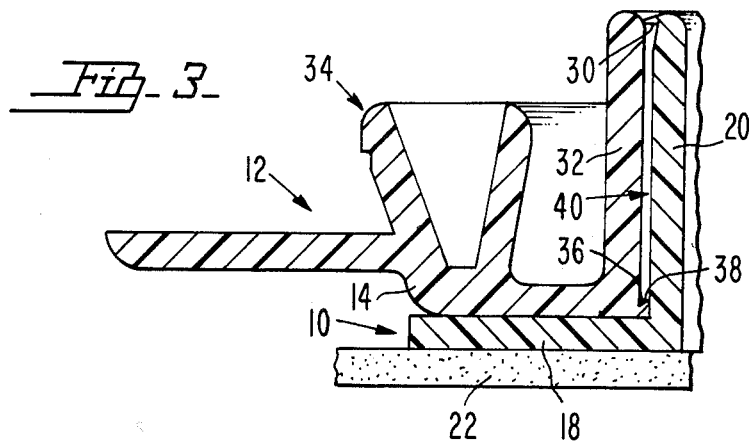
FIG. 3 is an axial section through a body side member showing the parts of FIGS. 1 and 2 in their mutually contracted position.
Figure 4:
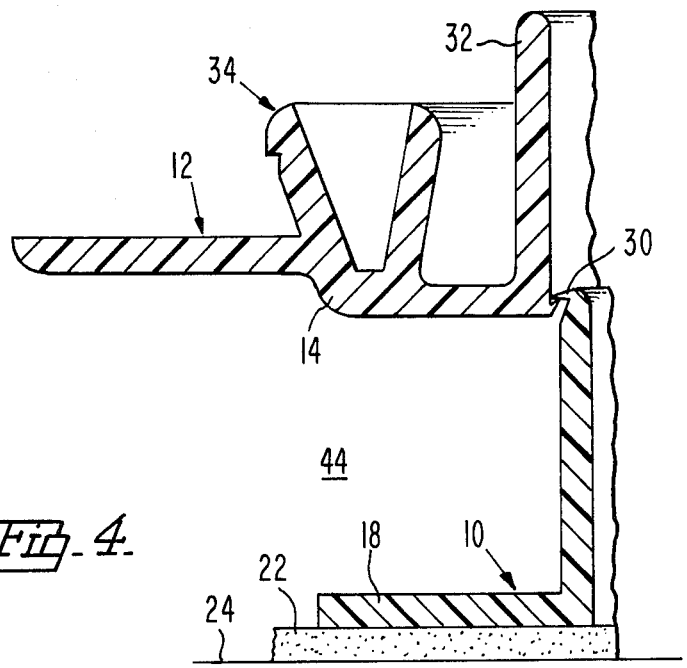
FIG. 4 is a similar sectional view to FIG. 3 but showing parts of the body side member in their telescopically extended condition, to provide space behind the flange for a wearer of the ostomy appliance to place his or her thumb or fingers.

The body side ostomy member illustrated in FIGS. 1-4 includes a first part 10 (shown in FIG. 1) which is made captive to another (second) part 12 (shown in FIG. 2). These two parts 10, 12 are telescopically slidable relative to one another to provide access for the fingers or thumb of a wearer beneath a lateral flange 14 on the second part 12, when the parts 10, 12 are in their telescopically extended condition, as shown in FIG. 4. The first part 10, as shown in FIG. 1, includes a laterally extending flange 18 and a substantially cylindrical wall 20. The flange 18 is, or can be, secured to a pad 22 of medical grade adhesive material, to thereby adhere the pad 22 to the skin 24 of the wearer of the ostomy appliance. In use, the adhesive pad 22 has a central stomal aperture 26 therein with which the stomal aperture 28 defined by the cylindrical wall 20 is substantially aligned in use. As illustrated, the flange 18 and the wall 20 are made in one piece. Alternatively, they may be made separately and suitably assembled together, e.g., with adhesive. The upper end of the cylindrical wall 20, as shown in the drawing, which is the outer end when the ostomy appliance is being worn, has an outwardly radially extending resilient flexible peripheral seal strip 30 which extends completely around the wall 20 encircling the aperture 28. The second part 12 has a substantially cylindrical wall 32 encircling the stomal aperture 28. In the preferred embodiment of the invention, the wall 32 is integral with the flange coupling element 34. The wall 32 is also integral with a radially inwardly extending resilient flexible peripheral seal strip 36, which is dimensioned so that its rim 38, which is spaced from the wall 32 engages the external surface 40 of the wall 32. The effect of the seal strips 30, 36 is to make the first part 10 captive to the second part 12 once these parts 10, 12 have been assembled together. They also permit the second part 12 to slide telescopically relative to the wall 20 of the first part 10.

As a preferred embodiment of the invention, an upper peripheral region of the wall 20 is recessed or rebated so as to allow the seal strip 30 to move inwardly. This is useful when the parts are being assembled as the second part 12 can then be placed over and pushed down on the cylindrical wall 20 of the first part 10. Once assembled, the seal strips 30 and 36 spring resiliently outwardly in the case of seal strip 30 and inwardly in the case of seal strip 36, so engaging the opposed surface and mutually guiding the parts 10 and 123 for limited telescopically sliding relationship.

In the contracted position of the body side member, shown in FIG. 3, the radially inner part of the flange 14 rests on the flange 18. In the telescopically extended condition of these parts 10, 12, as shown in FIG. 4, the part 12 has been slid away from the body of the wearer thereby allowing ample space 44 for a user to place his fingers or his thumb behind the flange 14, in order to permit attachment of an ostomy bag to the second part 12 without any significant pressure being applied to the tender stomal or peristomal region.

As illustrated, the coupling element 34 preferred in the present invention is a coupling element substantially as disclosed and illustrated in U.S. patent application Ser. No. 758,920, filed July 25, 1985.

The coupling element construction and operation will be better understood from the following description.

Figure 5:
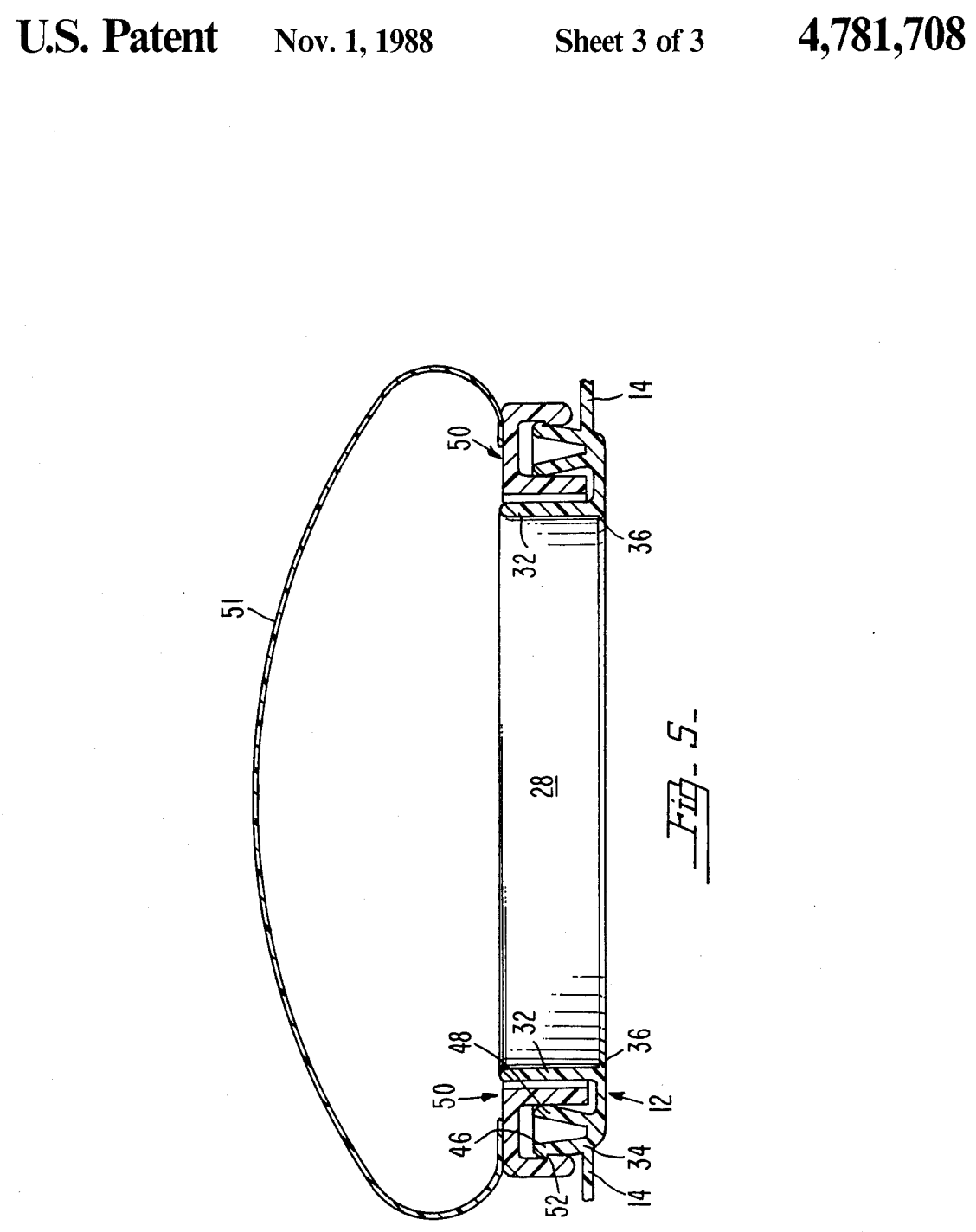

Referring now to FIGS. 2 and 5, the second part 12 has a flange 14 with circular stomal orifice 28 therein. The flange 14 is made in one piece with a coupling element 34. This is formed by two diverging ribs 46 and 48. The ribs 46, 48 are joined adjacent to the flange 14 and diverge in a direction away from the plate. As shown in cross-section, the ribs 46, 48 define a V-formation which encircles the wall 32.

The wall 32 serves as a chute 22 which conducts discharged waste directly into the interior of an ostomy bag 51 and prevents such waste from becoming lodged in recessed or crevices in the interengaged coupling elements.

With continued reference to FIG. 5, the manner in which a body side coupling part 12 can be interengaged with a bag side coupling element 50 is illustrated. As can be seen, an internal rim 52 on the element 50 snaps over the rib 46 and is received in a recess defined by a stepped formation comprising L-shaped flat surfaces on the rib 46. This engagement maintains the coupling elements 12 and 50 securely connected together so that the bag 51 is securely connected to the two part body side member 10, 12. Due to the small radial overlap and the inherent flexibility of the plastic used, the coupling elements 34 and 50 may be manually separated easily, even by elderly or infirm persons. Moreover, the bag side member 12 and the body side member 10 may be reconnected without discomfort, because the user can place his fingers or thumbs behind the flange 14 when the bag side member 12 is in its telescopically extended condition, and then press the two members together manually. In this process, no significant force is applied inwardly towards the abdomen so avoiding pain or discomfort.

In a particular embodiment of the invention, the angle between the surfaces 56 and 58 of the respective 46, 48 may be about 40°. The axial length of the surface 66 may be about 0.010 inch (0.25 mm) and the radial extent of the surface 68 may be about 0.0084 inch (0.203 to 0.213 mm) and preferably should not be less than 0.008 inch.

The preferred plastics material for the parts 10 and 12 is low density polyethylene and this may have a Shore A hardness which is conventional in couplings of the kinds shown in U.S. Pat. No. 4,460,363 entitled OSTOMY BAG which issued to P. L. Steer, et al. on July 17, 1984.

While a particular embodiment of the invention has been particularly described and illustrated, it will be understood that modifications may be made without departing from the invention.

For example, instead of the peripheral strips 30 and 36, there could be an O-ring or a pair of O-rings disposed between the outer surface of the wall 20 and the inner wall of the part 32. This O-ring could be adhesively attached to one or other part, or could be lodged in a peripheral channel in either of these parts. Similarly, with two O-rings, one could be lodged in a peripheral channel in each part.

It will be realized that there is no permanent physical connection between the part 10 and the part 12, unlike prior art ostomy appliances utilizing the so-called "accordion-flange" arrangement (e.g. British Patent Application No. 2,115,288 A). Moreover, there is no intrusion of parts of the appliance into the stomal orifice region, which is significant advantage in terms of comfort in wear.

Figure 6:
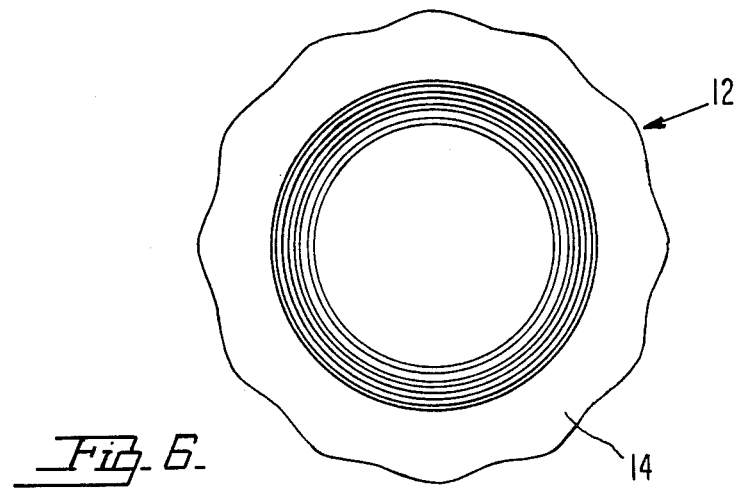
FIG. 6 is a front view of a flange for use in the invention.

While the outer edge of the flange 14 may be circular, it may alternatively have cut-outs or be scalloped shape. This is helpful in permitting it to be gripped by the user and facilitates relative rotation of the parts 10 and 12 if this is required to make the telescopic inward and outward movement easier. FIG. 6 is a front view illustrating a scalloped edge on the flange 14.

It will be understood that the thickness and shape of the flexible strips may be varied from that illustrated; also the inherent flexibility of the plastics material employed may be adjusted as appropriate by using conventional plasticizers.

I claim:

1. A body side ostomy member which includes a medical grade adhesive pad and a coupling ring means, said coupling ring means consisting of inner and outer concentric member means which are captive and slide telescopically with respect to another forming an integral coupling means, said inner concentric member means having a flange means with a resilient, flexible sealing strip means distal to said pad, said outer member means having a resilient flexible sealing strip means on a proximal end of said outer member means such that when the inner and outer member means are longitudinally extended apart with respect to each other, said sealing strip means limits the telescopic sliding movement of said outer and inner concentric member means and provides a space between said member means to enable a user's thumb or fingers to be placed therebetween.

2. An ostomy member according to claim 1 in which said inner and outer concentric means have first and second walls which are parallel to and slideable with respect to one another, said inner concentric member including a stomal orifice which is substantially circular, and said first and second walls are substantially cylindrical.

3. An ostomy member according to claim 2 in which the first and second walls are located one within the other for telescopic sliding movement and the movement is limited by an arrangement of cooperating parts which also serve a sealing or anti-leakage function.

4. An ostomy member according to claim 3 in which one wall, the innermost is provided with an outwardly extending resilient flexible peripheral seal strip, and other wall, the outermost, is provided at its other end with an inwardly extending resilient flexible peripheral seal strip, each of these seal strips extending towards, and such that its distal portion engages the confronting surface of the other wall.

5. An ostomy member according to claim 4 in which the walls are substantially coaxial cylinders sliding one within the other and the inner is connected to (or integral with) the flange which is secured to the medical grade adhesive pad.

6. An ostomy member according to claim 2 in which the first and second walls are located one within the other for telescopic sliding movement and the movement is limited by an arrangement of cooperating prats which also serve a sealing or anti-leakage function.

7. An ostomy member according to claim 6 in which one wall, the innermost is provided with an outwardly extending resilient flexible peripheral seal strip, and other wall, the outermost, is provided at its other end with an inwardly extending resilient flexible peripheral seal strip, each of these seal strips extending towards the other, such that the distal portion of each engages the confronting surface of the other wall.

8. An ostomy member according to claim 7 in which the walls are substantially coaxial cylinders sliding one within the other and the inner is connected to (or integral with) the flange which secured to the medical grade adhesive pad.

* * * * *

UNITED STATES PATENT AND TRADEMARK OFFICE
CERTIFICATE OF CORRECTION

PATENT NO. : 4,781,708
DATED : November 1, 1988
INVENTOR(S) : Peter L. Steer

It is certified that error appears in the above-identified patent and that said Letters Patent is hereby corrected as shown below:

Column 4, line 3, "123" should read --12--.

Column 6, line 32, "prats" should read --parts--.

Signed and Sealed this

Twenty-fifth Day of April, 1989

Attest:

DONALD J. QUIGG

*Attesting Officer*  *Commissioner of Patents and Trademarks*